United States Patent [19]

Monestier

[11] Patent Number: 4,685,929
[45] Date of Patent: Aug. 11, 1987

[54] TOTAL HAND PROSTHESES

[75] Inventor: Jacques Monestier, Valmondois, France

[73] Assignee: Compagnie Generale de Participations, S.A., Luxembourg; a part interest

[21] Appl. No.: 744,094

[22] PCT Filed: Sep. 28, 1984

[86] PCT No.: PCT/FR84/00212
§ 371 Date: Jun. 28, 1985
§ 102(e) Date: Jun. 28, 1985

[87] PCT Pub. No.: WO85/01437
PCT Pub. Date: Apr. 11, 1985

[30] Foreign Application Priority Data
Oct. 5, 1983 [FR] France ................... 83 15850

[51] Int. Cl.$^4$ .............................................. A61F 2/54
[52] U.S. Cl. ........................................................ 623/64
[58] Field of Search ................... 623/57, 64; 414/1, 4, 414/7; 901/30, 39, 45

[56] References Cited
U.S. PATENT DOCUMENTS
39,578 8/1863 Kimball ................................. 623/57
984,179 2/1911 Aydt ..................................... 623/64
3,188,753 6/1965 Lovercheck ........................ 623/64

FOREIGN PATENT DOCUMENTS
1324097 3/1963 France .................................. 623/64
2236478 2/1975 France .................................. 623/64
7423597 2/1976 France .................................. 623/64
509230 2/1957 Italy ..................................... 623/64

Primary Examiner—Richard J. Apley
Assistant Examiner—James Prizant
Attorney, Agent, or Firm—Browdy and Neimark

[57] ABSTRACT

A hand prosthesis or artificial hand with soft gripping having a palmar part made from a flexible material, and an attached dorsal part formed from a rigid material having a base plate having a dorsal face, and a palmar face forming a palm of the hand, and fingers detachably attached to the base plate on its dorsal face, with each finger having ball joint elements; a return spring is connected to a hook and passes internally through the joints over dorsal facing sides of pins, tubular guides are supportedly mounted and attached to the internal walls of the joints, traction spring segments in the tubular guides have spaced portions between ends of succeeding segments with the spaced portions occurring in zones of the ball joint elements, a traction cable is connected to the hook and guided internally of the joints and passes through the tubular guides within the traction spring elements, a yoke is connected to a single traction cable to balance forces and divide the force from the single traction cable into four decreasing forces to initiate movement of the fingers in order, and a thumb is detachably attached to the base plate.

17 Claims, 7 Drawing Figures

TOTAL HAND PROSTHESES

BACKGROUND OF THE INVENTION

1. Field of the Invention

The present invention relates to an improved hand prosthesis or artifical hand.

2. Description of the Prior Art

French Pat. No. 73 25719 of the July 13, 1973 in the name of the applicant proposed an artifical hand which comprises a metal or plastic skeleton, with articulated phalanges, covered with molded rubber foam coated with a reinforced elastomer skin with, on its back part, traction springs which return the fingers into the open position and with, on its palmar portion, nylon threads which slide in flexible sheaths and are attached to the phalanges or top joints, the three phalanges of each finger (two for the thumb) being articulated together without lateral play for the thumb, the forefinger, the middle finger and with lateral play for the ring finger and the little finger, and the palm of the hand comprises a base piece, integral with a ball joint for orientating the wrist and forming two metacarpals for the thumb and the forefinger, and three metacarpals for the middle finger, the ring finger, the little finger, fixed resiliently to the base piece. Furthermore, the certificate of addition No. 74 23597 of the July 8 1974, to the above patent, describes among other things an improvement in which the thumb is lockable manually in several positions and pivots on an oblique gusset carried by the base piece, with a spring pawl and teeth providing the locking.

Of course the articulated phalange prosthesis known from this patent and certificate of addition has numerous advantages and, in particular, provides an artificial hand capable of very elaborate gripping, it has however a certain number of disadvantages which the applicant has sought to remedy. In fact, in the artifical hand of the prior art represented by these publications, some of the mechanical parts (traction springs) are associated with the dorsal or back part and others (the articulation threads); with the palmar part of the prosthesis. This forms a considerable disadvantage for manufacture, since the dorsal portion, the palmar portion and the mechanical parts of the prosthesis are manufactured separately then assembled together to form the prosthesis. This also forms a serious drawback in the case where, because of wear thereof or a malfunction, the mechanical parts of the prosthesis must be repaired or replaced. Since an operation on the prosthesis for repairing or replacing mechanical parts concerns both the dorsal and palmar portions of the prosthesis it is therefore complicated and expensive. In addition, in the known prosthesis, the fingers are integral with the base piece mentioned above, which forms the palm of the prosthesis so that if one of the fingers becomes defective and unusable, it is the whole of the mechanism which must be replaced.

SUMMARY OF THE INVENTION

The aim of the present invention is therefore to provide an artifical hand which answers better the requirements of practice than the artifical hand proposed earlier by the applicant, in particular in that the arrangement of the mechanical parts is rationalized, so that they are integrally secured only in a single portion of the prosthesis, which portion may if required be temporarily removed from the other portion, for repair or replacement, the fingers of the artifical hand being able to be removed individually for replacement in the case of wear, breakage or deficiency.

The present invention therefore provides a so called soft gripping artificial hand, which is formed in two parts, namely a dorsal part made from an appropriate rigid material, with which the mechanical articulation pieces of the artifical hand are associated, and a palmar part made from a flexible material adapted for ensuring gripping comfort and perfect adaptation to the object, the dorsal and palmar parts being secured together by any appropriate removable means, such as clipping, socketing, tenon and mortice fitting, bonding, especially.

In a preferred embodiment of the invention, the dorsal part of the artifical hand comprises, in combination:

A flat base plate which plays the role of by screwing. partial finger prostheses by means of a piece playing the role of metacarpal ball joint, which finger prostheses are each formed, for the four fingers replacing the fore finger, the middle finger, the ring finger and the little finger, from three elements juxtaposed in the longitudinal direction, molded so as to have the structure of the dorsal and lateral parts of the corresponding finger and articulated with respect to each other about "ball joints" situated at the distal end of the first and second molded elements whereas the prothesis of the thumb is formed by molding a single piece to the shape of the dorsal part and of the lateral parts of the thumb., means for articulating, with respect to each other, the three juxtaposed elements which form each of the four above mentioned fingers and define a phalange, a middle joint and a top joint, which articulation means comprise, for each finger: a traction cable fixed at its distal end to a hook or similar element secured to the internal (or palmar) face of the distal end of each top joint and at its proximal end to the assymmetrical arms of an assymmetrical arm force balancer situated on the dorsal face side of said dorsal portion of the prosthesis; the passage of the carries from the palmar face of each of the partial finger prostheses carried by said dorsal part to the dorsal face. This latter being provided by means of through slide supports corresponding to each cable, carried by said base plate a slide fixed to the bottom of the palmar face of each of the elements forming the phalanges, middle joints and top joints, in which is mounted a traction spring segment in which the traction cable slides, the length of each spring segment being such that the successive segments have a discontinuity on ach side of a transverse articulation pin carried by the corresponding ball joint of an element (phalange, middle joint or top joint), with respect to said ball joint, the adjacent ends of two successive traction spring segments playing the role of stop for limiting the bending angle of the interphalange articulations.

In an advantageous arrangement of this embodiment, each finger prosthesis with three articulated phalanges is provided with a return spring fixed at its distal end to an internal hook provided at the distal end of each top joint and emerging at its opposite end, on the dorsal face, through an orifice formed in each piece playing the role of metacarpal ball joint, which spring is provided in the vicinity of said opposite end with an appropriate adjustment system.

In another advantageous arrangement of this embodiment, a second slide is juxtaposed with the first one, in the phalange of at least one of the four above mentioned fingers, and guides the passage of a second cable in said phalange, which presents said phalange from rising when the thumb and fingers in question are in opposition.

In yet another advantageous arrangement of this embodiment, each transverse articulation axis of a phalange, middle joint or top joint on the corresponding ball joint of the phalange which precedes it in the longitudinal direction comprises a spacer tube which ensures uniform spacing between the return spring and the interphalange articulation plane.

In another advantageous arrangement of this embodiment, the partial dorsal thumb prosthesis is articulated so as to be placed in opposition with the other fingers, by means of a mechanism comprising a mobile plate substantially perpendicular to the base plate, fixed at one of its ends to the internal face of the thumb prosthesis and whose opposite end is engaged between two fixed plates carried directly or indirectly by the base plate, one of these two fixed plates having a ratchet wheel profile in the notches of which is engaged a pawl connected by a spring to a pivoting support, and return springs disposed substantially parallel to the mobile and fixed plates and connecting the first one to each of the second ones, bringing the thumb back to the rest position.

In yet another advantageous arrangement of this embodiment, the force balancer to which the proximal ends of each traction cable of the fingers are fixed receives, in addition, the end of the single traction cable which controls the operation of the artificial hand of the invention, whose other end is connected to a physical control means such as the shoulders of the wearer of the prosthesis, by means of a harness, or to a mechanical control means, such as an electric, pneumatic or hydraulic cylinder.

In an advantageous embodiment, this force balancer comprises a main arm substantially in the form of a stirrup or U, each of whose ends carries a secondary arm, each of which receives the traction cables corresponding to two of the fingers, a traction eye integral with the main arm and disposed off center with respect to the axis of symmetry of said arm serving for securing the traction cable which controls the operation of the four fingers.

According to the invention, the purpose of the assymmetric arm force balancer, is to distribute the single traction force which is transmitted thereto in four decreasing forces, from the fore finger to the little finger, and thus to initiate movement of the fingers in the order providing the best gripping quality (fore finger, middle finger, ring finger, little finger).

In yet another arrangement of the invention, the artificial hand of the present invention is provided with a system for locking the prosthesis in the position closed on an object.

Such a locking system preferably comprises a U shaped body in the bottom of which passes the traction cable and in which is pivotably mounted on a pin a locking lug and a device controlling the locking lug formed by a screw or by an eccentric lever pivoting on a pin.

Stressing of the control device causes the lug to be clamped against the traction cable and locks it at the bottom of the U shaped body, and release of said control device frees the control cable which then slides freely in said U shaped body.

In accordance with the invention, the palmar portion of the artifical hand is made from a flexible material such as elastomer foam, covered with a skin and is replaceable in the case of wear by separating the dorsal part carrying the mechanical pieces, by simple removal.

Also in accordance with the invention, a pawl joint connection for removably mounting the artifical hand at the level of the wrist, is fixed to the proximal end of the base plate.

In addition to the preceding arrangements, the invention further comprises other arrangements which will be clear from the following description.

The present invention relates more particularly to the artificial hands in accordance with the preceding arrangements, taken by themselves or for fitting an amputee with an artifical hand.

BRIEF DESCRIPTION OF THE DRAWINGS

The invention will be better understood from the complement of description which follows with reference to the accompanying drawings in which.

It will of course be readily understood that these drawings and the corresponding descriptive parts are given solely by way of illustration of the object of the invention, of which they form in no way a limitation.

DESCRIPTION OF THE PREFERRED EMBODIMENTS

The artifical hand of the present invention comprises a dorsal part 1 with which are associated the mechanical articulation parts of said prosthesis, which dorsal part 1 is formed by molding, from a rigid high mechanical strength material, such as metal (bronze, steel), from an appropriate plastic material, from carbon fibers, etc. . . . , and a palmar part 2 made from a flexible material, more especially from rubber foam covered with skin, which ensures a "soft" grip providing gripping comfort and good adaptation to the object, desired by prosthesis wearers.

Figure 1:
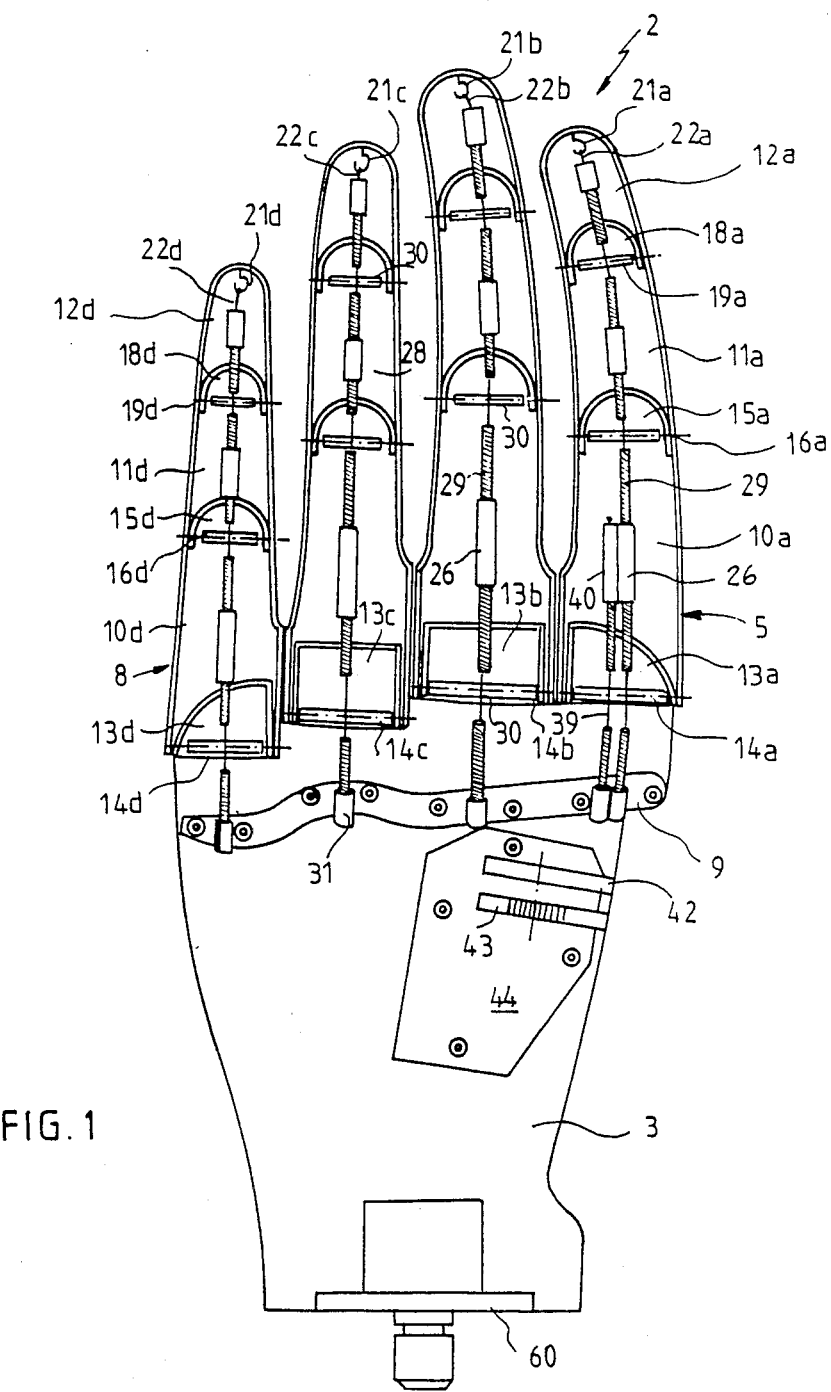
FIG. 1 is a top view of the palmar face of the dorsal part of an artifical hand in accordance with the invention.
Figure 2:
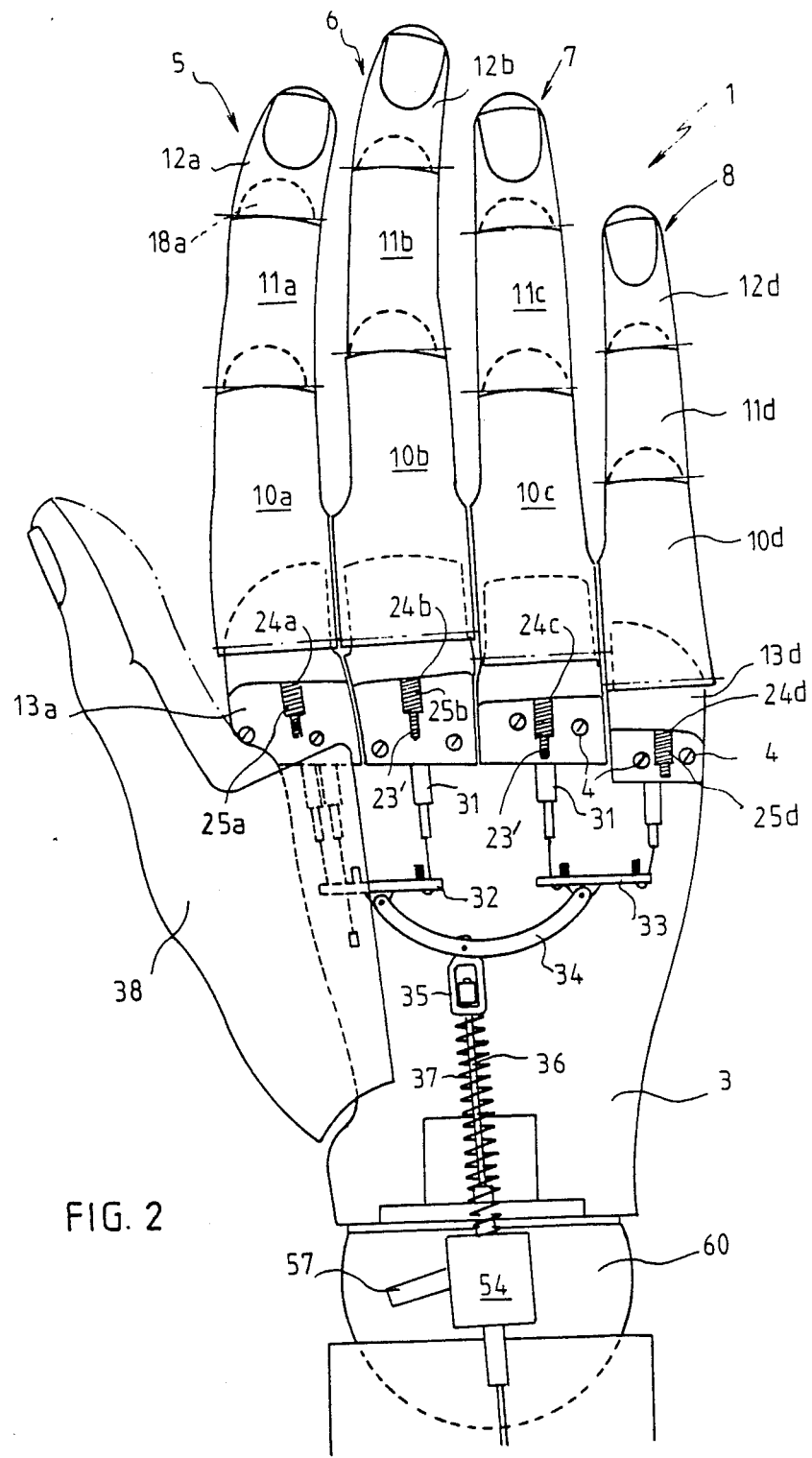
FIG. 2 is a top view of the dorsal face of the dorsal part of an artifical hand in accordance with the invention.
Figure 3:
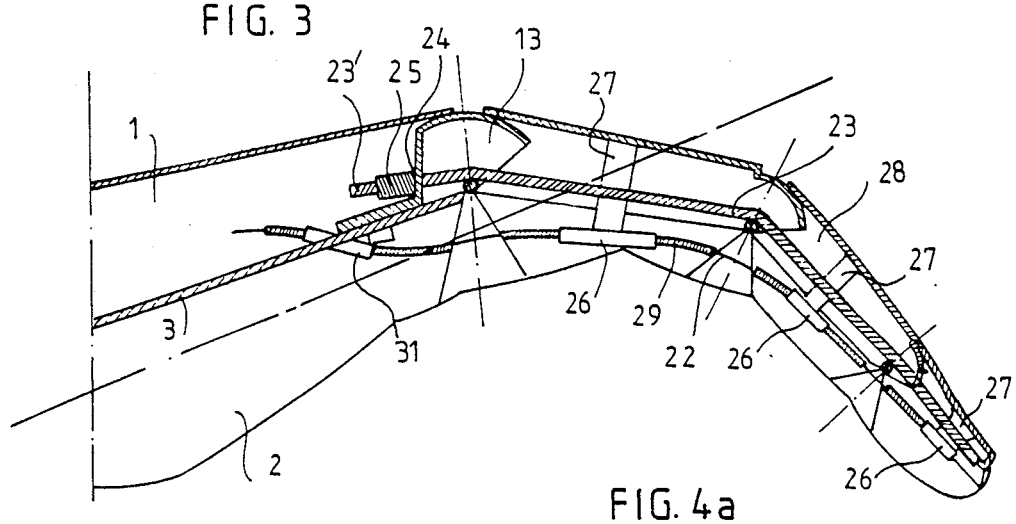
FIG. 3 is a sectional view of a finger of a prosthesis according to the invention.

The dorsal part 1 comprises a base plate 3 to the dorsal face of which are fixed, by means of screws 4, four fingers namely a forefinger 5, a middle finger 6, a ring finger 7 and a little finger 8. The fingers 5 to 8 fixed by means of screws 4 are consolidated in their mount by means of a fixing bar 9 carried by the palmar face of said dorsal part 1, into which emerge the ends of screws 4. The fingers 5 to 8 each comprise three longitudinally juxtaposed elements, 10a-11a-12a to 10d-11d-12d which are articulated with respect to each other, as will be explained further on, and these fingers are each fixed to the base plate 3 by means of a metacarpal "ball joint" 13a to 13d fixed to said plate 3 by the screws 4. The elements 10a to 10d which form the phalanges of fingers 5 to 8 are mounted on the metacarpal ball joint 13a-13d by means of a horizontal pin 14a-14d; each phalange 10a to 10d comprises at its end opposite the one fixed to pin 14a–14d, a ball joint 15a–15d in which is mounted a pin 16a–16d for articulating the element 8, and which is terminated at its opposite distal end by a ball joint 18a–18d, which in its turn carries a pin 19a–19d for articulating the element 1 2a–12d which forms the top joint of each finger 5–8. Each of these top joints 12a–12d comprises at its internal distal end, i.e. on its palmar face, a hook 21a–21d to which are fixed on the one hand a traction cable 22a–22d and on the other separate return springs 23 with only ends 23′ shown in FIG. 2 for each finger in a variant, two separate hooks may be provided for fixing the traction cable and the return spring, respectively.

23 emerges, in the vicinity of its opposite end 23′, on the dorsal face of said dorsal 1 of the artifical hand of the invention, through an orifice 24a–24d formed in the metacarpal "ball joint" 13a–13d; this return spring 23 is provided with an adjustment system 25a–25d.

The traction cable 22a–22d is guided in each finger 5–8 by tubular slides 26 each mounted on support 27 integrally molded with the dorsal part 1 or welded to the bottom 28 of fingers 5–8. A tubular slide 26 supported by a support 27 is provided in association with each of the phalanges, middle joints and top joints. The traction cable 22a–22d further slides in traction spring segments 29 crimped in the tubular slides 26 so that in the rest position of the prosthesis the traction cable is free of any guiding, in a zone 30, which corresponds to the zone of the articulation ball joints 13a–13d, 15a–15d and 18a–18d. Each cable 22a–22d passes through the base plate 3 through slide supports 31 welded to the base plate 3 or integrally molded therewith, so as to reach the dorsal face of the dorsal part 1 of the prosthesis, where each cable 22a–22d is fixed to the secondary asymmetric arms 32–33 of a force balancer, themselves carried by a main arm 34 which has, off centered with respect to its axis of symmetry, an eye 35 for securing the traction cable 36 which controls the articulation of the four fingers 5–8 under the effect of a single traction force communicated by shoulder movements made by the wearer of the prosthesis, itself connected to the shoulders by a harness, or by an electric, pneumatic or hydraulic cylinder (not shown). A compression spring 37 which surrounds the traction cable 36 neutralises the friction of this latter in the sheath.

The eye 35 is off centered in the direction of the thumb 38, so as to divide up the single traction force communicated by cable 36 into four decreasing forces, from the fore finger to the little finger, and thus to initiate the movement of the fingers in the order providing the best gripping quality, namely: fore finger, middle finger, ring finger, little finger.

Each of the pins 14a–14d, 16a–16d and 18a–18d for articulating the phalanges, middle joints and top joints with respect to each other comprises a small spacer tube which provides uniform spacing of the return spring 23a–23d with respect to the interphalange articulation plane.

The fore finger 5 comprises an additional traction cable 39 guided in a slide 4 juxtaposed with slides 36 and integral, like this latter, with the bottom of the phalange 10a, which cable 39 prevents the phalange 10a from rising when the thumb 38 and forefinger 5 are in opposition.

Thumb 38 is moved by a mechanism which allows it to be placed in different positions in opposition to the other fingers. This mechanism comprises a plate 41 substantially perpendicular to the base plate 3, and secured to thumb 38 by screws (not shown). At its end opposite the one which is secured to the thumb. plate 41 is engaged between two plates 42–43 which are situated in planes parallel to the plane bf said plate 41. These plates 42–43 are fixed to the base plate 3 either directly (by welding or by integral molding), or indirectly by means of a plate 44. Plate 41, which is mobile, is fixed to a shaft 45 between the fixed plates 42–43, the lower plate 43 of which has a ratchet wheel profile in the notches 46 of which is engaged a pawl 47 fixed to the lower face of plate 41 and connected by a spring 48 to a pivoting support 49, the engagment of pawl 47 with one or other of the notches 46 bringing the thumb at will into opposition with any one of the other four fingers. Two return springs 50 fixed on the one hand to two pegs 52 on plate 44 (or base plate 3) and on the other hand to two pegs 53 on the mobile plate 41 return thumb 38 to the rest position.

Figure 4A:
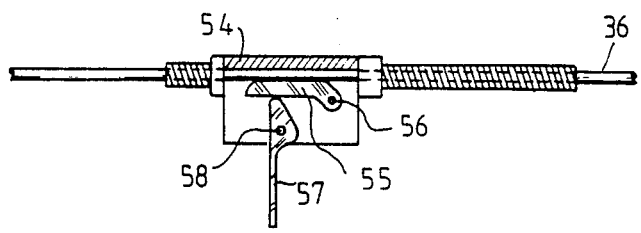
FIGS. 4a and 4b and FIG. 5 show in axial section a device for locking the prosthesis in position.
Figure 4B:
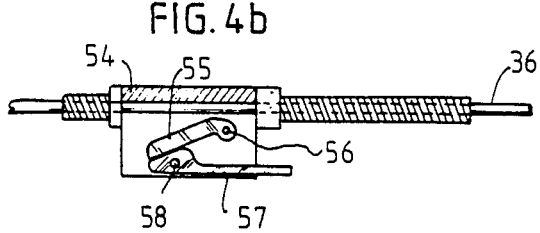
Figure 6:
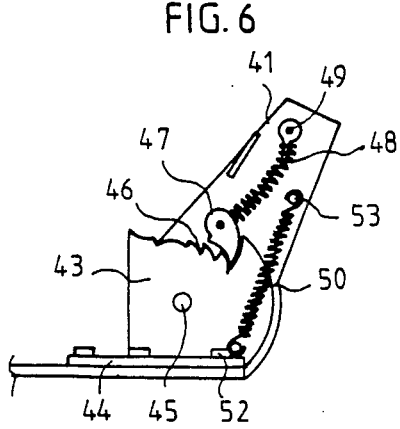
FIG. 6 is a bottom view of the device for moving the thumb into a position of opposition.
Figure 5:
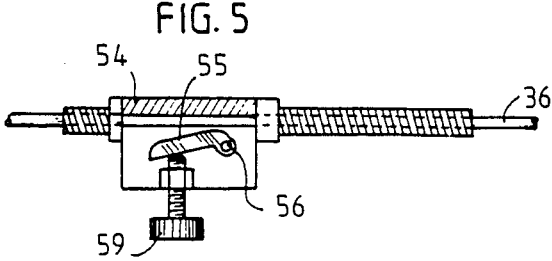

A locking system allows the prosthesis to be locked in the position closed on an object (for example on a pen for writing); in the embodiment shown in FIGS. 4a and 4b and 5, the system comprises a U shaped body 54 in the bottom of which the traction cable 36 slides., a locking lug 55 pivoting about a pin 56 between the legs of the U; a locking member such as the eccentric lever 57 pivoting about the pin 58 between the legs of the U (cf. FIGS. 4a and 4b) or such as a locking screw 59 (fc. FIG. 5) causes lug 58 to be clamped against the traction cable 36 which is locked at the bottom of the U shaped body 54. Unlocking of the cable 36 is provided by freeing lug 55 by actuating lever 57 or unscrewing screw 59.

A ball jqint connection 60 for mounting the prosthesis at the level of the wrist is fixed by means of screws to the base plate 3 and the locking system 54–58 or 59 may be advantageously fixed to said connection 60.

For aesthetic reasons, the base plate, the ball joint connections 60 and the force balancer are hidden by a cover fixed to the base plate 3 and to the fingers of the prosthesis, to which it may be articulated.

Actuation of the articulation cables 22a–22d causes articulation of the phalanges with respect to each other, the bending angle of the interphalange articulations being however limited by the reciprocal abutment effect exerted when the facing ends of two traction spring segments 29 come into contact.

Since the fingers are fixed by screws, they may be readily replaced in the case of need, and similarly since the palmar 2 and dorsal 1 parts are assembled together by a socket fit or similar, one or other of these parts may be readily replaced without difficulty and without requiring an artificial limb repairer.

The design of the artifical hand in accordance with the invention allows:

manufacture thereof on an industrial scale,
repair thereof under considerably simplified conditions, not requiring a specialist;
fitting an artificial hand to amputees having a long stump, while keeping the natural supination, because all the mechanical parts are housed inside the artifical hand and control it, for the same reasons by means of a single control cable.

Although the artifical hand of the invention has only been described above in its prosthetic use, it will be readily understood that it may find a particularly interesting use in robotization where, placed at the end of a robotized arm, it may be used very extensively because of its high gripping precision allowing it to be used in particular for gripping and classifying loose objects of indeterminate shape, for handling heavy and bulky objects, more particularly in the field of construction from prefabricated elements, its use for the remote controlled handling of objects in a hostile environment, its use in spatial vessels and satellites or diving saucers, etc. . . . , its medical and industrial uses not excluding its use for constructing robots or similar works.

As is obvious from the foregoing, the invention is in no wise limited to those of its embodiments and modes of application which have been described more explicitly; it embraces on the contrary all variants thereof which may occur to the technician skilled in the matter, without departing from the scope or spirit of the present invention.

What is claimed is:

1. A hand prosthesis or artificial hand with so called soft gripping comprising
   A. a dorsal part formed from a rigid material having mechanical means for articulating the hand associated therewith;
   B. a palmar part made from a flexible material adapted for ensuring gripping comfort and adaptation to an object being handled;
   C. said dorsal and palmar parts detachably attached to each other;
   D. said dorsal part including
      a. a base plate having a dorsal face and a palmar face and forming a palm of the hand,
      b. fingers including a forefinger, a middle finger, a ring finger, and a little finger, each of said fingers detachably attached to said base plate on its dorsal face,
      c. each said finger including
         (a) ball joint elements,
         (b) three longitudinally juxtaposed elements forming a lower joint, a middle joint, and a top joint, articulated with respect to each other and to said base plate by respective said ball joint elements,
         (c) said ball joint elements further comprising pin means articulating said joints,
         said pin means being positioned internally in said respective ball joint elements and spaced from a dorsal surface of said dorsal part,
         a hook means located in an internal distal end of said top joint,
         a return spring connected to said hook means and passing internally through said top, middle, and lower joints over dorsal facing sides of said pin means respectively and beneath dorsal surfaces of said joints,
         tubular guides supportedly mounted and attached to the internal walls of said top, middle, and lower joints,
         traction spring segments in said tubular guides having spaced portions between ends of succeeding segments with said spaced portions occurring in zones of said ball joint elements,
         a traction cable connected to said hook means and guided internally of said joints, passing through said tubular guides within said traction spring segments, and in the rest position of the hand, said traction csable being free of guidance in said zones of said ball joint elements, and with the end of said traction cable away from said hook means passing through said base plate to said dorsal face of said base plate,
      (d) force balancing means on said dorsal face of said base plate connected to a single traction cable means in control the articulation of said finger under the effect of a single traction force,
      (e) each said traction cable from said finger connected to connecting means attached to said force balancing means,
      (f) said force balancing means including a yoke type means and said connecting means to divide up said single traction force communicated bysaid single traction cable means into four decreasing forces from said forefinger to said little finger and initiate the movement of said fingers in an order from forefinger, middle finger, ring finger, to little finger,
      (g) and a thumb detachably attached to said base plate.

2. The artificial hand as claimed in claim 1 wherein said fingers are fixed to said base plate by screws.

3. The artificial hand as claimed in claim 1 further comprising
   means to adjust the tension of said return spring on the end of said return spring opposite from said hook means.

4. The artificial hand as claimed in claim 1 further comprising
   additional traction cable means to prevent said lower joint of said forefinger from rising when said thumb and said forefinger are in opposition including
      a. a second tubular guide supportedly mounted and attached to the internal wall of said lower joint of said forefinger in juxtaposition to said tubular guide supporting said traction cable passing through all said joints of said forefinger,
      b. a traction spring segment in said second tubular guide through which said additional traction cable means passes,
      c. said additional traction cable passing through said base plate to said dorsal face of said base plate and connected to said force balancing means.

5. The artificial hand as claimed in claim 1 further comprising
   A. a ball joint connection detachably connected to said base plate for mounting the hand at the level of the wrist,
   B. a locking system fixed to said ball joint connection,
   C. a compression spring means attached between said force balancing means and said locking system,
   D. said single traction cable means passing through said locking system.

6. The artifical hand as claimed in claim 5 further comprising
   said locking system including
      a. a U shaped body with said single traction cable means passing adjacent said U shaped body,
      b. a locking lug pivotally mounted on the opposite side of said single traction cable means from said U shaped body,
      c. and means to pivot said locking lug a against said single traction cable means.

7. The artificial hand as claimed in claim 6 further comprising said means to pivot said locking lug being an eccentric lever pivotally mounted for contacting and pivoting said locking lug agaisnt said single traction cable means.

8. The artificial hand as claimed in claim 6 further comprising said means to pivot said locking lug being a locking screw having an end contacting said locking lug to pivot said locking lug against said single traction cable means.

9. The artificial hand as claimed in claim 1 wherein said force balancing means includes
   a. said yoke type means asymmetrically connected to said single traction cable means at a point on said yoke type means nearer to the end closest to the forefinger,
   b. said connecting means including secondary asymmetrical arms pivotally connected asymmetrically on each end of said yoke type means,
   c. said traction cables from said little and ring fingers connected to said secondary asymmetrical arms and said traction cables from said middle and forefinger connected to the other of said secondary asymmetrical arms,
   d. said one of said secondary asymmetrical arms pivotally connected to said yoke type means at a point closer to the connection of said secondary arm with said traction cable from said ring finger,
   e. said other of said secondary asymmetrical arms pivotally connected to said yoke type means at a point closer to the connection of said secondary arm with said traction cables from said forefinger.

10. The artificial hand as claimed in claim 1 wherein said traction spring segments are limiting means by forming abutments in said zones to limit the bending angle of the articulations between said joints.

11. The artificial hand as claimed in claim 1 wherein said thumb includes
   a. means to move the thumb in opposition to the said fingers,
   b. said moving means including
      (a) a first plate substantially perpendicular to said base plate and secured to said thumb,
      (b) second and third plates fixed to said base plate and in planes parallel to said first plate and on opposite sides of said first plate,
      (c) a shaft through said first plate and connected to said second and third plates for pivotal movement of said first plate,
      (d) said second plate having a rachet wheel profile of notches,
      (e) a pawl fixed to said first plate for engagement in said rachet wheel profile of notches,
      (f) a pivotal support connected to said first plate,
      (g) a spring means connecting said pawl to said pivotal support to bring said thumb into opposition with at least one of said fingers,
      (h) return springs means connected to said base plate and to said first plate to return said thumb to a rest position.

12. The artificial hand as claimed in claim 11 further comprising
   a locking system including
      a. a U shaped body with said single traction cable means passing adjacent said U shaped body,
      b. a locking lug pivotally mounted on the opposite side of said single traction cable means from said U shaped body,
      c. and means to pivot said locking lug against said single traction cable means.

13. The artificial hand as claimed in claim 12 further comprising said means to pivot said locking lug being an eccentric lever pivotally mounted for contacting and pivoting said locking lug against said single traction cable means.

14. The artificial hand as claimed in claim 12 further comprising said means to pivot said locking lug being a locking screw having an end contacting said locking lug to pivot said locking lug against said single tration casble means.

15. The artificial hand as claimed in claim 1 wherein each said finger is further including
   (a) three longitudinally juxtaposed elements articulated with respect to each other forming a lower joint, a middle joint, and a top joint,
   (b) a metacarpal ball joint element connected to said base plate,
   (c) a first horizontal pin connecting said lower joint to said metacarpal ball joint element,
   (d) a second ball joint element on the opposite end of said lower joint from which it is connected to said first horizontal pin,
   (e) a second horizonal pin connected for articulating said middle joint about said second ball joint element,
   (f) a third ball joint element on the opposite end of said middle joint from which it is connected to said second horizontal pin,
   (g) a third horizontal pin connected for articulating said top joint about said third ball joint element,
   (h) said first, second, and third horizontal pins positioned internally in said respective ball joint elements and spaced from a dorsal surface of said dorsal part.

16. The artificial hand as claimed in claim 1 wherein
   A. said second and third ball joint elements of said fingers are spherical portions extending from said middle and lower joints witn the adjacent ends of said top and middle joints slidable over the outer surface of said spherical portions,
   B. and said metacarpal ball joint element is a spherical portion with the adjacent end of said lower joint slidable over the outer surface of said spherical portion of said last mentioned ball joint element.

17. The artificial hand as claimed in claim 16 wherein partial areas of said spherical portions form parts of the dorsal surface of the hand when the hand is in the closed or partially closed position.

* * * * *